United States Patent
Zorman et al.

(10) Patent No.: US 11,458,309 B2
(45) Date of Patent: Oct. 4, 2022

(54) FLEXIBLE IMPLANTABLE TISSUE STIMULATOR AND METHODS OF MAKING AND USING SAME

(71) Applicants: The United States Government as represented by the United States Department of Veterans Affairs, Washington, DC (US); CASE WESTERN RESERVE UNIVERSITY, Cleveland, OH (US)

(72) Inventors: Christian Zorman, Euclid, OH (US); Douglas Shire, Ithaca, NY (US); David Keicher, Los Ranchos, NM (US); Katherine M. Bogie, Shaker Heights, OH (US)

(73) Assignees: United States Government as Represented by the Department of Veterans Affairs, Washington, DC (US); Case Western Reserve University, Cleveland, OH (US)

( * ) Notice: Subject to any disclaimer, the term of this patent is extended or adjusted under 35 U.S.C. 154(b) by 0 days.

(21) Appl. No.: 16/648,031

(22) PCT Filed: Sep. 19, 2018

(86) PCT No.: PCT/US2018/051618
§ 371 (c)(1),
(2) Date: Mar. 17, 2020

(87) PCT Pub. No.: WO2019/060332
PCT Pub. Date: Mar. 28, 2019

(65) Prior Publication Data
US 2020/0254246 A1 Aug. 13, 2020

Related U.S. Application Data

(60) Provisional application No. 62/560,551, filed on Sep. 19, 2017.

(51) Int. Cl.
*A61N 1/36* (2006.01)
*A61N 1/05* (2006.01)
(Continued)

(52) U.S. Cl.
CPC ....... *A61N 1/36003* (2013.01); *A61N 1/0509* (2013.01); *A61N 1/0514* (2013.01);
(Continued)

(58) Field of Classification Search
CPC .. A61N 1/36003; A61N 1/08; A61N 1/37217; A61N 1/37229; A61N 1/37252; A61N 1/3787
See application file for complete search history.

(56) References Cited

U.S. PATENT DOCUMENTS

| 7,970,450 B2 | 6/2011 | Kroecker et al. |
| 2009/0157147 A1 | 6/2009 | Cauller et al. |

(Continued)

FOREIGN PATENT DOCUMENTS

| WO | WO-2008/080073 A2 | 7/2008 | |
| WO | WO-2008080073 A2 * | 7/2008 | ............. A61N 1/372 |

(Continued)

OTHER PUBLICATIONS

U.S. Appl. No. 61/594,105, filed Feb. 2, 2012, Kath M. Bogie (U.S. Government, Represented by the Dept. of V.A.).
(Continued)

*Primary Examiner* — Eric D. Bertram
(74) *Attorney, Agent, or Firm* — Ballard Spahr LLP

(57) ABSTRACT

Provided are devices and methods for providing a flexible implantable tissue stimulator. A flexible implantable tissue stimulator can be use in a variety of medical/surgical procedures, and therapeutic interventions, such as musculoskeletal stimulation therapy. The flexible implantable tissue stimulator can be implanted via a minimally invasive pro-
(Continued)

cedure and comprises a biocompatible flexible construction that enables it to conform to a variety of implantation orientations and biological conditions. The flexible implantable tissue can provide programmable biphasic electrical stimulation to impaired tissue, such as a gluteal muscle.

20 Claims, 8 Drawing Sheets

(51) Int. Cl.
  *A61N 1/372* (2006.01)
  *A61N 1/378* (2006.01)
  *A61N 1/08* (2006.01)
(52) U.S. Cl.
  CPC ............ *A61N 1/08* (2013.01); *A61N 1/3601* (2013.01); *A61N 1/36007* (2013.01); *A61N 1/3611* (2013.01); *A61N 1/36053* (2013.01); *A61N 1/36071* (2013.01); *A61N 1/3787* (2013.01); *A61N 1/37217* (2013.01); *A61N 1/37229* (2013.01); *A61N 1/37252* (2013.01)

(56) References Cited

U.S. PATENT DOCUMENTS

| | | | |
|---|---|---|---|
| 2009/0242854 A1* | 10/2009 | Li | C09D 11/101 252/519.33 |
| 2010/0241057 A1 | 9/2010 | Pak et al. | |
| 2011/0009924 A1* | 1/2011 | Meskens | A61N 1/36038 607/57 |
| 2011/0034977 A1* | 2/2011 | Janik | H01L 24/24 607/116 |
| 2011/0112601 A1* | 5/2011 | Meadows | A61N 1/3605 607/42 |
| 2012/0190956 A1 | 7/2012 | Connolly | |
| 2014/0046398 A1* | 2/2014 | Sachs | A61N 1/36071 607/46 |
| 2014/0163641 A1 | 6/2014 | Yao et al. | |
| 2014/0206947 A1 | 7/2014 | Isserow | |
| 2015/0112179 A1* | 4/2015 | Malackowski | A61N 1/37217 600/377 |
| 2015/0343205 A1* | 12/2015 | Howard | A61N 1/372 607/46 |
| 2016/0074664 A1 | 3/2016 | De Ridder | |
| 2016/0101282 A1 | 4/2016 | Bergelin | |
| 2016/0220135 A1* | 8/2016 | Negi | A61B 5/296 |
| 2016/0339239 A1 | 11/2016 | Yoo et al. | |
| 2017/0043164 A1 | 2/2017 | Biele et al. | |
| 2017/0117087 A1* | 4/2017 | Ridler | A61N 1/3787 |

FOREIGN PATENT DOCUMENTS

| | | | | |
|---|---|---|---|---|
| WO | WO-2009/046366 A1 | | 4/2009 | |
| WO | WO-2009046366 A1 | * | 4/2009 | ......... A61N 1/36003 |

OTHER PUBLICATIONS

U.S. Appl. No. 14/363,277 (U.S. Pat. No. 9,320,907), filed Jun. 5, 2014 (Apr. 26, 2016), Kath M. Bogie (U.S. Government, Represented by the Dept. of V.A.).
U.S. Appl. No. 14/675,270 (U.S. Pat. No. 10,201,703), filed Mar. 31, 2015 (Feb. 12, 2019), Kath M. Bogie (U.S. Government, Represented by the Dept. of V.A.).
U.S. Appl. No. 16/229,530, filed Dec. 21, 2018, Kath M. Bogie (U.S. Government, Represented by the Dept. of V.A.).
U.S. Appl. No. 62/560,551, filed Sep. 19, 2017, Kath M. Bogie (U.S. Government, Represented by the Dept. of V.A.).
PCT, PCT/US2018/051618 (WO 2019/060332), Sep. 19, 2018 (Mar. 28, 2019), Kath M. Bogie (U.S. Government, Represented by the Dept. of V.A.).
POSiFECT(Biofisica) Non patent literature/product, accessed on May 1, 2015. URL: <http://www.wounds-uk.com/journalarticles/bio-electrical-stimulation-therapy-using-posifectrd>.
Procellera Wound Dressing Non patent literature/product, accessed on May 1, 2015. URL: <http://procellera.com/procellera/technology>.
Various Devices, Including GV350 model (Biomedical Life Systems) Non patent literature/product, accessed on May 1, 2015.
Wound EL (Mölnlycke Health Care) Non patent literature/product, accessed on May 1, 2015. URL: <http://www.molnlycke.com/advanced-wound-care-systems/electrical-stimulation/#confirm>.
International Search Report and Written Opinion dated Jan. 28, 2019 by the International Searching Authority for Patent Application No. PCT/US2018/051618, which was filed on Sep. 19, 2018 and published as WO 2019/060332 dated Mar. 28, 2019 (Inventor—Zoman et al.; Applicant—The United States Governement as Represented by the United States Department of Veterans Affairs) (15 pages).

* cited by examiner

FLEXIBLE IMPLANTABLE TISSUE STIMULATOR AND METHODS OF MAKING AND USING SAME

CROSS-REFERENCE TO RELATED APPLICATION

This is a U.S. National Phase Application of International Application No. PCT/US2018/051618, filed Sep. 19, 2018, which claims priority to and the benefit of the filing date of U.S. Provisional Patent Application No. 62/560,551, filed on Sep. 19, 2017, which is incorporated herein by reference in their entireties.

FIELD

This invention generally relates to devices and methods used for musculoskeletal therapy.

BACKGROUND

A spinal cord injury (SCI) can leave an individual with limited to non-existent mobility, resulting in a need for extensive therapy and interventions for musculoskeletal health. For example, as a consequence of impaired mobility after an SCI, an individual may develop pressure ulcers (PU) and/or deep tissue injury (DTI) from sitting or lying in place. Electrical stimulation applied to the surface of an individual's skin often requires excessive charge and/or fails to penetrate the individual's surface tissue enough to stimulate deep tissue to reduce PUs and DTIs. Further, repeated application of electrodes to the same surface of the individual's skin can cause skin damage. These and other shortcomings are addressed by the devices and methods set forth herein.

SUMMARY

It is to be understood that both the following general description and the following detailed description are examples and explanatory only and are not restrictive. Provided are devices and methods for providing a flexible implantable tissue stimulator. A flexible implantable tissue stimulator is described for use in a variety of medical/surgical treatments and/or procedures, such as gluteal muscle stimulation and the like. The flexible implantable tissue stimulator can comprise dimensions that enable it to be implanted in an individual via a minimally invasive procedure. For example, the flexible implantable tissue stimulator can be inserted into a subcutaneous pocket through a 25.5 millimeter (one inch) incision in an individual. The flexible implantable tissue stimulator can provide user and/or clinician defined electrical stimulation to exercise regions of impaired and/or paralyzed muscle tissue. For example, exercise of paralyzed gluteal muscle tissue can improve the intrinsic health of the tissue at a seating interface by reducing regional interface pressures (e.g., static sitting pressures in a sacro-ischial region, etc.) and increasing regional blood flow. The flexible implantable tissue stimulator can comprise flexible hybrid electronics disposed on a flexible liquid crystal polymer (LCP) substrate, and a biocompatible flexible encapsulate with non-metallic layers. The flexible implantable tissue stimulator, based on the non-metallic encapsulate layers, can be safe for magnetic resonance imaging (MRI) when implanted in an individual. The flexible construction of the flexible implantable tissue stimulator enables it to conform to various shapes (e.g., a body shape or a tissue surface, etc.) and positions when implanted in the body of an individual without causing rigid points where erosion of tissue and/or device material can occur.

A flexible implantable tissue stimulator can comprise an inductive power transceiver that provides power to one or more pattern generation nodes. The one or more pattern generation nodes can generate one or more patterns based on muscle stimulation pattern information received from the inductive power transceiver. The flexible implantable tissue stimulator can comprise and/or be connected to (e.g., in communication with, etc.) one or more electrodes. The one or more patterns generated by the pattern generation nodes can correspond to one or more electrical pulses transmitted by the one or more electrodes to tissue, such as gluteal muscle tissue and the like. For example, the one or more electrodes can comprise portions that can be placed in close proximity and/or touching a motor point or a nerve associated with impaired tissue. The close proximity placement of the electrodes can reduce a level of electrical charge required to stimulate the nerve. A reduced electrical charge requirement can enable the flexible implantable tissue stimulator to operate with minimal power consumption. Minimal power consumption can enable the flexible implantable tissue stimulator to be reliable and simple to use long-term, on a day-to-day basis, to maintain hypertrophy of tissue damaged due to a SCI, such as paralyzed gluteal muscles, for example.

Additional advantages will be set forth in part in the description which follows or may be learned by practice. The advantages will be realized and attained by means of the elements and combinations particularly pointed out in the appended claims.

BRIEF DESCRIPTION OF THE FIGURES

The accompanying drawings, which are incorporated in and constitute a part of this specification, illustrate several aspects described below and together with the description, serve to explain the principles of the invention. Like numbers represent the same elements throughout the figures.

DETAILED DESCRIPTION

Figure 1:
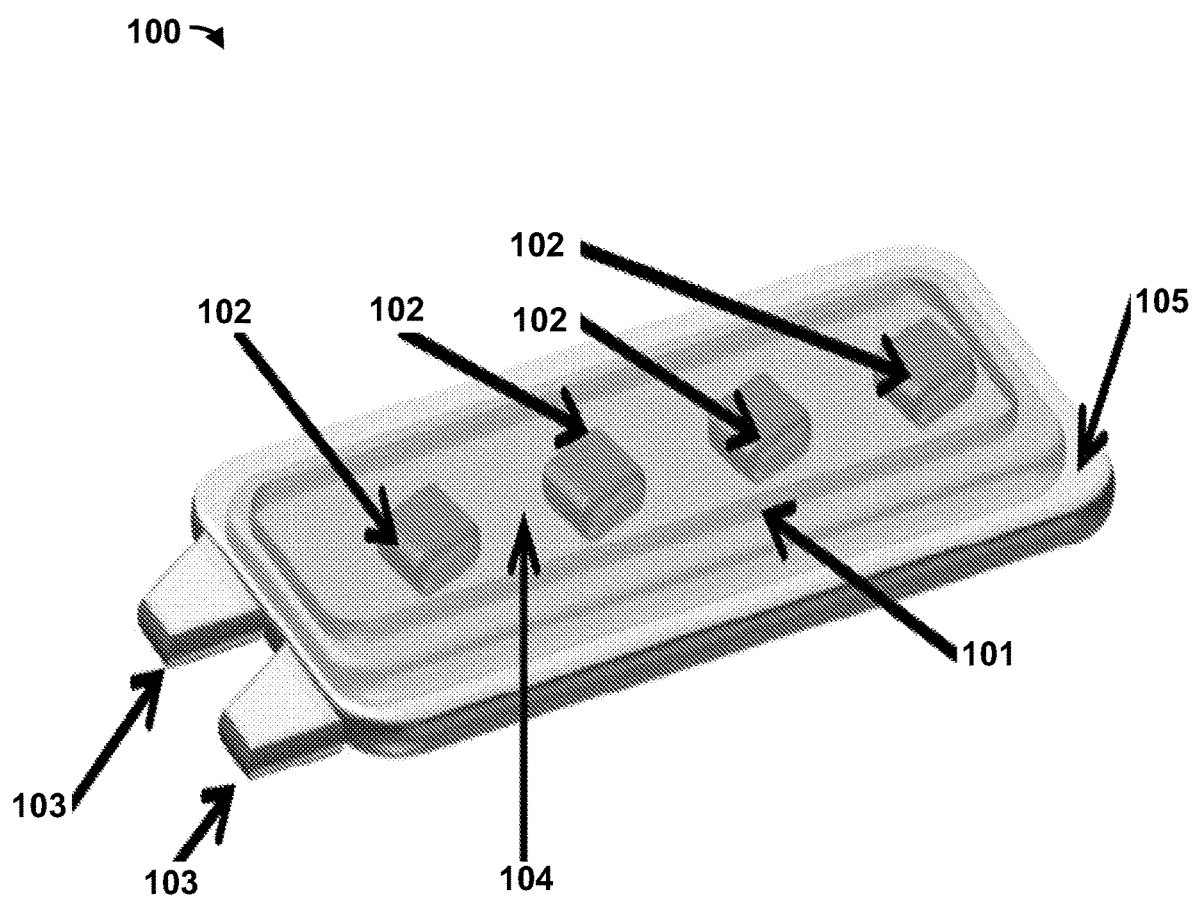
FIG. 1 is a diagram of an exemplary flexible implantable tissue stimulator as disclosed herein.

The present invention can be understood more readily by reference to the following detailed description, examples, drawing, and claims, and their previous and following description. Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "an electrode" can include two or more such electrodes unless the context indicates otherwise.

The word "or" as used herein means any one member of a particular list and also includes any combination of members of that list.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

As used herein, the term "proximal" refers to the portion of an element that is closest to the body of a subject when the element is operatively positioned according to its intended use.

As used herein, the term "distal" refers to the portion of an element that is farthest from the body of a subject when the element is operatively positioned according to its intended use.

As used herein, the terms "tissue" and "tissue region" refer to a selected tissue within the body of a subject, as well as the soft tissue surrounding and/or adjacent to a nerve and/or bone.

As used herein, the terms "individual" and "subject" are used interchangeably to refer to humans or animals.

As used herein, the term "patient" refers to an individual or subject who has been diagnosed with one or more conditions in need of treatment and/or therapy using the devices and methods disclosed herein.

Provided are devices and methods for providing flexible implantable tissue stimulator. A flexible implantable tissue stimulator is described for use in a variety of medical/surgical treatments and/or procedures, such as gluteal muscle stimulation and the like. A flexible implantable tissue stimulator may be used for various purposes, including, for example and without limitation, prevention of post-trauma muscle atrophy, treatment of chronic pain, treatment of hypertension, management of urinary incontinence, treatment of back pain, vagal neuromodulation, treatment of sleep apnea, and/or gastric electrical stimulation for treatment of gastrointestinal disorders, and the like. A flexible implantable tissue stimulator may be used as an aid in assisting an individual with injury or disease, such as damage to a central nervous system and/or peripheral nervous system to restore and/or assist movement. The flexible implantable tissue stimulator can comprise dimensions that enable it to be implanted in an individual via a minimally invasive procedure and positioned in a minimally invasive location. For example, the flexible implantable tissue stimulator, in fully packaged form, can comprise a length between 0 millimeters and 24 millimeters (e.g., less than about 24 millimeters or from about 12 millimeters to about 24 millimeters), a width between 0 millimeters and 12 millimeters (e.g., less than about 12 millimeters or from about 6 millimeters to about 12 millimeters), and a height (e.g., thickness, etc.) between 0 millimeters and 4 millimeters (e.g., less than about 4 millimeters or from about 2 millimeters to about 4 millimeters). Optionally, the flexible implantable tissue stimulator can have a maximum height (e.g., thickness) of less than 6 millimeters and a maximum weight of less than 25 grams. Although exemplary dimensions are disclosed herein, it is contemplated that the flexible implantable tissue stimulator can comprise any dimensions suitable for use as disclosed herein. The flexible implantable tissue stimulator can be inserted into a subcutaneous pocket through a 25.5 millimeter (one inch) incision in an individual. The flexible implantable tissue stimulator can provide user and/or clinician defined electrical stimulation to exercise regions of impaired and/or paralyzed muscle tissue. For example, exercise of paralyzed gluteal muscle tissue can improve the intrinsic health of the tissue at a seating interface by reducing regional interface pressures (e.g., static sitting pressures in a sacro-ischial region, etc.) and increasing regional blood flow.

A flexible implantable tissue stimulator can comprise electronics (optionally, flexible electronics) disposed on a flexible substrate, such as a liquid crystal polymer (LCP) substrate and/or the like. Optionally, the electronics can comprise flexible hybrid electronics. As used herein, the term "flexible hybrid electronics," abbreviated as "(FHE)" refers to electronic devices that are constructed from individual rigid electronic components (e.g., ASIC chips, capacitors, inductors, etc.) that are bonded or secured to a flexible substrate that supports electronic interconnects and other flexible electronic structures to form a miniaturized flexible electronic circuit. Flexible hybrid electronics are distinct from integrated electronics which would be formed on a single 'chip' or integrated circuit. Exemplary electronics include, without limitation, an inductive power transceiver, one or more pattern generation nodes, and the like. Optionally, in addition to the flexible substrate, all or portions of the electronics can also be flexible. Thus, in exemplary aspects, a flexible implantable tissue stimulator can comprise flexible components (e.g., flexible hybrid electronics, etc.) disposed on a flexible substrate. Optionally, it is contemplated that the flexible implantable tissue stimulator can comprise a flexible hybrid electronics (FHE) core with an overall dimensional footprint of about 20 millimeters long, about 8 millimeters wide, and less than 2 millimeters high (thick) together with flexible packaging to provide an overall package thickness of 4 millimeters. Magnetic resonance imaging (MRI) compatible silver nanoparticle ink or any other suitable ink, dye, and/or connection medium can be used to connect/interconnect the electronics.

A flexible implantable tissue stimulator can comprise a biocompatible flexible encapsulating structure with one or more (optionally, a plurality of) non-metallic layers. For example, electronic components (e.g., flexible hybrid electronics, etc.) disposed on a flexible substrate (e.g., LCP substrate, etc.) can be coated with at least one layer (optionally, multilayers) of a flexible material to encapsulate the electronic components. Optionally, the flexible material can be applied to encapsulate the flexible implantable tissue stimulator via vapor deposition, spin casting, dip coating, molding, and/or any other means commonly used to deposit a curable material that is dispensed in liquid form. For example, the flexible material can comprise polymers such as polydimethylsiloxane, parylene-C, and/or the like. Further, the flexible material can comprise inorganic insulators, such as aluminum oxide grown by atomic layer deposition, for example.

In some embodiments and/or examples, mechanical protection may be required to protect rigid components (e.g., an ASIC, etc.), and medical-grade epoxy can be dispensed at specific locations prior to application of the flexible encapsulating structure. A lifetime of a flexible implantable tissue stimulator can be extended by a multilayered encapsulating structure that comprises two or more materials and multiple thin film layers. The multilayered encapsulating structure can further comprise interleaved stacks of the curable material and/or vapor deposited material. The multilayered encapsulating structure can ensure that a structural defect in any one layer that could cause the flexible implantable tissue stimulator to fail is terminated at an interface formed by a complementary layer of the multilayered encapsulating structure. The thicknesses of each layer of the multilayered encapsulating structure, as well as the total number of layers of the multilayered encapsulating structure, can be determined by assessing a desired flexibility (e.g., flexural modulus, etc.) of a flexible implantable tissue stimulator. The outermost layer of the multilayered encapsulating structure (e.g., encapsulate) can comprise a textured surface that enhances biocompatibility with tissue. The outermost layer can further comprise a soft material, such as polydimethylsiloxane to enhance biocompatibility.

It is contemplated that the flexible implantable tissue stimulator, based on the layer(s) of flexible material, can be safe for (and compatible with) magnetic resonance imaging (MRI) when implanted in an individual. For example, MRI compatibility can be characterized according to American Society for Testing and Materials (ASTM) standards F2052 (Standard Test Method for Measurement of Magnetically Induced Displacement Force on Medical Devices in the Magnetic Resonance Environment) and F2213 (Standard Test Method for Measurement of Magnetically Induced Torque on Medical Devices in the Magnetic Resonance Environment).

Flexible construction of the flexible implantable tissue stimulator can enable it to conform to various shapes (e.g., a body shape or a tissue surface, etc.) and positions when implanted in the body of an individual without causing rigid points where erosion of tissue and/or device material can occur. For example, the flexible implantable tissue stimulator can conform to an arc from a 0 centimeter radius to a 38 centimeter radius (e.g., average male calf radius, etc.). However, it is contemplated that the flexible implantable tissue stimulator can conform to an arc of any radius that is suitable for use within the body of a subject as disclosed herein. The flexible implantable tissue stimulator, based on the flexible encapsulating structure and disposition of the flexible components, can comprise any suitable flexural modulus.

A flexible implantable tissue stimulator can comprise an inductive power transceiver that provides power to one or more pattern generation nodes (e.g., one or more dedicated application-specific integrated circuits (ASICs), etc.). Optionally, in exemplary aspects, it is contemplated that the one or more pattern generation nodes can comprise a plurality of pattern generation node, such as, for example, two, three, four, five, six, seven, eight, or more pattern generation nodes. The inductive power transceiver (e.g., inductive power and/or data coil(s), etc.) can be any suitable transceiver (e.g., coil(s), etc.), such as a printed nanoparticle ink coil that enables bidirectional communication (e.g., wireless communication, radio frequency (RF) communication, amplitude modulated signals, etc.) and power transmission (e.g., inductive power transmission, rechargeable power transmission, etc.). The inductive power transceiver can receive power (e.g., an induced voltage, etc.) from an external transceiver (e.g. a control module comprising the external transceiver, etc.). The external transceiver can comprise an inductive coil and/or the like. For example, the external transceiver can generate magnetic fields that induce the inductive power transceiver of the flexible implantable tissue stimulator to generate voltage. The magnetic fields can be frequency shift keyed (FSK) to encode data, such as pattern generation data, that is received by the inductive power transceiver and provided to the one or more pattern generation nodes. For example, the pattern generation data can cause the one or more pattern generation nodes to generate biphasic charge-balanced stimulation patterns with adjustable amplitude and timing. The pattern generation data (or any other data) can be communicated to the flexible implantable tissue stimulator (e.g., the one or more pattern generation nodes, etc.) at any rate, such as at a rate of at least 565 Kbps, for example. The inductive power transceiver can receive inductive power from the external transceiver (e.g. a control module comprising the external transceiver, etc.) over a distance (e.g., 25 millimeters or any selected distance). It is contemplated that the external transceiver can be electrically powered by a rechargeable battery, with the external transceiver being configured to supply at least three days of electrical stimulation (at 10 hours a day) on a single battery charge.

Additionally, or alternatively, it is contemplated that the flexible implantable tissue stimulator can comprise a rechargeable power source (e.g., a rechargeable battery, etc.) that provides power to the one or more pattern generation nodes. For example, the rechargeable power source can comprise a lithium ion battery, a super capacitor, or any other suitable device/component suitable for rechargeable power generation.

The inductive power transceiver can communicate information/data (e.g., telemetry data, diagnostic data, etc.) bi-directionally to a computing device, display device, and/or the like. The inductive power transceiver can communicate (e.g., transmit, etc.) information/data to a computing device, display device, and/or the like used to monitor power supply voltage, device operational status, tissue status/damage, electrode impedance, and/or the like. The computing device, display device, and/or the like can comprise a graphical user interface (GUI) user to generate pattern information and/or monitor power supply voltage, device operational status, tissue status/damage, electrode impedance, and/or the like associated with a flexible implantable tissue stimulator.

The one or more pattern generation nodes can be dedicated application-specific integrated circuits (ASICs) and/or the like. The one or more pattern generation nodes can be any type of integrated circuit or the like suitable for generating user defined pulse stimulation patterns. The one or more pattern generation nodes can operate independently or synchronously. Optionally, the one or more pattern generation nodes can be configured to selectively operate either independently or synchronously (in response to user and/or clinician input as further disclosed herein). When operating independently, it is contemplated that a plurality of nodes (for example, four nodes) can provide a plurality of channels (for example, four channels) of independently controlled electrical stimulation. The one or more pattern generation nodes can generate one or more patterns based on muscle stimulation pattern information received from the inductive power transceiver. For example, the one or more patterns can correspond to one or more asynchronous electrical stimulation pulses generated at any frequency (e.g., 20 Hertz, etc.) and/or duty cycle (e.g., a 15-second on, 15-second off pulse stimulation with a 17 minute rest interval, etc.). More generally, it is contemplated that the stimulation activity can have an active duty cycle ranging from about 10 seconds to about 15 seconds on and about 10 seconds to about 15 seconds off for a period of three minutes (or other selected duration), with a rest period ranging from about 0 minutes to about 20 minutes (optionally, from about 5 minutes to about 15 minutes or from about 10 minutes to about 15 minutes or from about 10 minutes to about 20 minutes). Optionally, in exemplary aspects, the stimulation activity can further comprise a pulse duration of about 0 to about 4 milliseconds (optionally, about 1 to about 3 microseconds or about 2 to about 4 microseconds) with an increment of about 5 microseconds, an amplitude ranging from about 0.5 to about 20 milliamps at an increment of about 0.15 milliamps, and a frequency ranging from about 1 to about 400 pulses per second at an increment of 1 pulse per second. Although specific amplitudes, frequencies, and increments are disclosed herein, it is contemplated that other amplitudes, frequencies, and increments can be used to provide stimulation as disclosed herein. The flexible implantable tissue stimulator can comprise operational current amplifiers that increase currents of the one or more patterns generated by the one or more pattern generation nodes.

The flexible implantable tissue stimulator can comprise and/or connect to (e.g., be in communication with, etc.) one or more electrodes (e.g., intramuscular electrodes, etc.). The one or more electrodes can comply with industry standards. For example, the one or more leads can comprise one or more of IS-1 type connector ports, DF-1 type connector ports, combinations thereof, or the like. The one or more patterns generated by the pattern generation nodes can correspond to one or more electrical pulses transmitted by the one or more electrodes to stimulate tissue, such as gluteal muscle tissue and the like. For example, the one or more electrodes can comprise portions that can be placed in close proximity and/or touching a motor point or a nerve associated with impaired tissue. The close proximity placement of the electrodes can reduce a level of electrical charge required to stimulate the nerve. A reduced electrical charge requirement enables the flexible implantable tissue stimulator to operate with minimal power consumption. Minimal power consumption enables the flexible implantable tissue stimulator to be reliable and simple to use long-term, on a day-to-day basis, to maintain hypertrophy of tissue damaged due to a SCI, such as paralyzed gluteal muscles, for example.

FIG. 1 shows an example flexible implantable tissue stimulator 100 according to the present devices and methods. The flexible implantable tissue stimulator 100 can comprise an inductive power transceiver 101. The inductive power transceiver 101 can be a printed nanoparticle ink coil, which can optionally be printed on a substrate as further described herein. The inductive power transceiver 101 can enable bidirectional communication (e.g., wireless communication, radio frequency (RF) communication, amplitude modulated signals, etc.) and power transmission (e.g., inductive power transmission, rechargeable power transmission, etc.) between the flexible implantable tissue stimulator 100 and an external control module. The external control module can be a computing device, an inductive power transceiver, a power supply, combinations thereof, and the like. The inductive power transceiver 101 can receive power (e.g., an inductive voltage, etc.) from the external control module. For example, the external control module can generate magnetic fields that induce the inductive power transceiver 101 to generate voltage. The magnetic fields can be frequency shift keyed (FSK) to encode data, such as pattern generation data, that is received by the inductive power transceiver 101 and provided at least one pattern generation node (optionally, a plurality of pattern generation nodes) 102. For example, the pattern generation data can cause the one or more pattern generation nodes to generate biphasic charge-balanced stimulation patterns with adjustable amplitude and timing. Pattern generation data (or any other data) can be communicated to the flexible implantable tissue stimulator 100 via the inductive power transceiver 101 and provided to the pattern generation nodes 102 at any rate, such as at a rate of at least 565 Kbps, for example. The inductive power transceiver 101 can receive inductive power from an external control module over a distance (e.g., 25 millimeters, etc.).

The pattern generation nodes 102 can be dedicated application-specific integrated circuits (ASICs) and/or the like. The pattern generation nodes 102 can be any type of integrated circuit or the like suitable for generating user defined pulse stimulation patterns. The pattern generation nodes 102 can operate independently or synchronously, or both independently and synchronously depending upon user selection/input as further disclosed herein. The pattern generation nodes 102 can generate one or more patterns based on muscle stimulation pattern information received from the inductive power transceiver 101. For example, the one or more patterns can correspond to one or more asynchronous electrical stimulation pulses generated at any frequency (e.g., 20 Hertz, etc.) and/or duty cycle (e.g., a 15-second on, 15-second off pulse stimulation with a 17 minute rest interval, etc.). The flexible implantable tissue stimulator 100 can comprise operational current amplifiers (not shown) that increase currents of one or more patterns generated by the pattern generation nodes 102.

The flexible implantable tissue stimulator 100 can comprise electrodes 103 that are in electrical communication with the pattern generation nodes 102. The electrodes 103 can be intramuscular electrodes. The electrodes 103 can comply with industry standards. For example, the electrodes 103 can comprise IS-1 type connector ports, DF-1 type connector ports, combinations thereof, or the like. One or more patterns generated by the pattern generation nodes 102 can correspond to one or more electrical pulses transmitted by the electrodes 103 to stimulate tissue, such as gluteal muscle tissue and the like. For example, the electrodes 103 can be placed in close proximity and/or touching a motor point or a nerve associated with impaired tissue. The close proximity placement of the electrodes 103 can reduce a level of electrical charge required to stimulate the nerve. A reduced electrical charge requirement can enable the flexible implantable tissue stimulator 100 to operate with minimal power consumption. Minimal power consumption enables the flexible implantable tissue stimulator to be reliable and simple to use long-term, on a day-to-day basis, to maintain hypertrophy of impaired tissue, such as paralyzed gluteal muscles, for example. In exemplary aspects, the tissue stimulator 100 can comprise a plurality of electrodes, such as, for example, two electrodes 103 as shown in FIG. 1. Optionally, as shown in FIG. 1, it is contemplated that the electrodes 103 can project outwardly from one or more end portions of the tissue stimulator 100.

The flexible implantable tissue stimulator 100 can comprise electronics (e.g., the inductive power transceiver 101, the pattern generation nodes 102, etc.), which can optionally be flexible and/or hybrid electronics, disposed on a flexible substrate 104. The flexible substrate 104 can be a liquid crystal polymer (LCP) substrate and/or the like. Magnetic resonance imaging (MRI) compatible silver nanoparticle ink or any other suitable ink, dye, and/or connection medium can be used to connect/interconnect the flexible hybrid electronics (e.g., the inductive power transceiver 101, the pattern generation nodes 102). Optionally, as shown in FIG. 1, it is contemplated that the inductive power transceiver 101 can be printed on a periphery of the substrate 104 and circumferentially surround (either completely or partially) the pattern generation nodes 102.

The flexible implantable tissue stimulator 100 can comprise a biocompatible flexible encapsulating structure 105. The flexible encapsulating structure 105 can comprise one or more (optionally, a plurality of) layers of a flexible material, such as polydimethylsiloxane, parylene-C, and/or the like that are applied to encapsulate at least a portion (optionally, all) of the electronics that are secured to the flexible substrate 104. For example, as shown in FIG. 1, it is contemplated that the flexible encapsulating structure 105 can include one or more layers of flexible material that are applied to a side of the substrate 104 opposite that of the power transceiver 101 and the pattern generation nodes 102, thereby encapsulating portions of the electrodes 103 and other electronic components (e.g., printed circuitry) located on that side of the substrate. Optionally, it is contemplated that one or more layers of flexible material can be applied over the power transceiver 101 and power generation nodes 102. Optionally, it is contemplated that the one or more layers of flexible material can be applied circumferentially in a 360-degree manner to encapsulate the tissue stimulator 101. Additionally, or alternatively, it is contemplated that one or more layers of flexible material can be printed on respective sides of the substrate 104 and joined together to provide the encapsulation disclosed herein. In exemplary aspects, the flexible encapsulating structure 105 can be applied to the flexible implantable tissue stimulator 101 via vapor deposition. The flexible implantable tissue stimulator 101, based on the multilayers of the flexible encapsulating structure 105, can be safe for magnetic resonance imaging (MRI) when implanted in an individual. MRI compatibility can be characterized according to American Society for Testing and Materials (ASTM) standards F2052 (Standard Test Method for Measurement of Magnetically Induced Displacement Force on Medical Devices in the Magnetic Resonance Environment) and F2213 (Standard Test Method for Measurement of Magnetically Induced Torque on Medical Devices in the Magnetic Resonance Environment).

Flexible construction of the flexible implantable tissue stimulator 100 can enable it to conform to various shapes (e.g., a body shape or a tissue surface, etc. . . . ) and positions when implanted in the body of an individual without causing rigid points where erosion of tissue and/or device material can occur. For example, the flexible implantable tissue stimulator 100 can conform to an arc from a 0 centimeter radius to a 38 centimeter radius (e.g., average male calf radius, etc.). The flexible implantable tissue stimulator 100 can conform to an arc of any radius. The flexible implantable tissue stimulator 100, based on the flexible encapsulate 105 and disposition of the flexible components (e.g., the inductive power transceiver 101, the pattern generation nodes 102, etc.), can comprise a flexural modulus of less than 200 MPa. The flexible implantable tissue stimulator 100, based on the flexible encapsulate 105 and disposition of the flexible electronic components (e.g., the inductive power transceiver 101, the pattern generation nodes 102, etc.), can comprise any flexural modulus.

Figure 2:
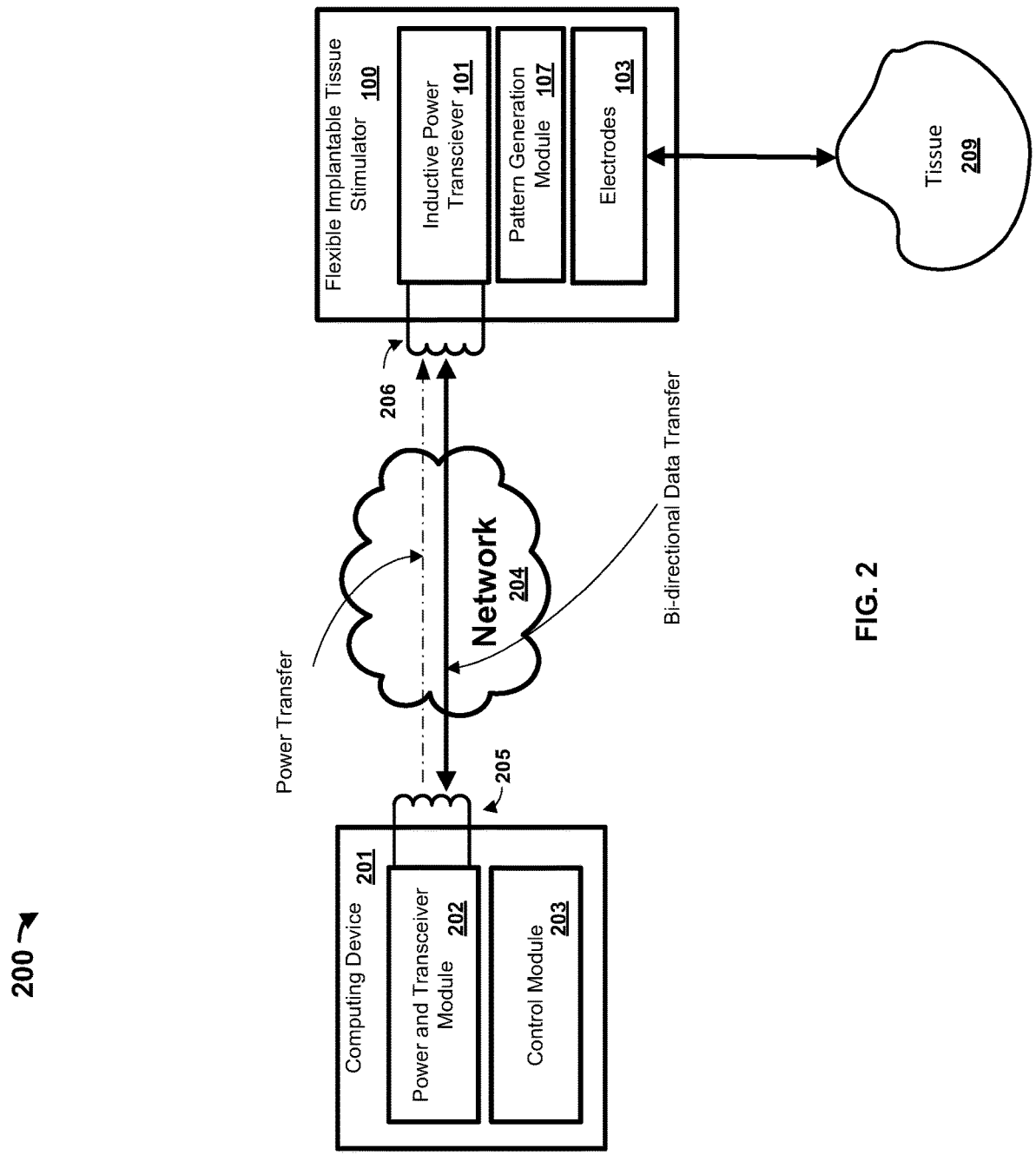
FIG. 2 depicts an exemplary system including a flexible implantable tissue stimulator as disclosed herein.

FIG. 2 shows a system 200 for a flexible implantable tissue stimulator. The system 200 can comprise a computing device 201 (e.g., a control device, a user interface, display device, etc.) in communication with a flexible implantable tissue stimulator 100 via a network 204. Various forms of communications can occur via the network 204. The computing device 201 can comprise a power and transceiver module 202. The power and transceiver module 202 can be a power source, power supply, rechargeable battery, combinations thereof, and the like. For example, the power and transceiver module 202 can comprise an inductive power transceiver with an inductive coil 205 that generates magnetic fields that can induce voltage on a receiving inductive power transceiver (e.g., an inductive coil 206, inductive power transceiver 101, etc.). The power and transceiver module 202 can transmit and receive data/information (e.g. encrypted data/information, etc.) via the network 204. For example, the power and transceiver module 202 can transmit/receive data/information to/from the flexible implantable tissue stimulator 100. The power and transceiver module 202 can receive data/information from a device via the network 204. The network 204 can comprise one or more magnetic fields, radio frequency (RF) transmissions, combinations thereof and the like. For example, the network 204 can comprise mutually-coupled radio frequency (RF) coil-generated transmissions/receptions, power and data transmissions at the same RF frequency or differing frequencies, infrared optical links, combinations thereof, and the like. The power and transceiver module 202 can receive data/ information from a device via one or more magnetic fields, radio frequency (RF) transmissions, optical links, combinations thereof and the like. For example, the power and transceiver module 202 can receive, via an inbound magnetic field, data/information that is frequency shift keyed (FSK) and transmitted at any rate (e.g., 565 Kbps, etc.).

The computing device 201 (e.g., a control device, a user interface, display device, etc.) can comprise a control module 203. The control module 203 can comprise a graphical user interface (GUI) that can be used to control devices, such as the flexible implantable tissue stimulator 100 and/or any other device. The GUI can be used to provide stimulation commands to the flexible implantable tissue stimulator, monitor operations and functions associated with the flexible implantable tissue stimulator, monitor one or more of the communications link and/or the electrodes associated with the flexible implantable tissue stimulator, and/or the like. The GUI can be used to monitor power supply voltage, device (e.g., the flexible implantable tissue stimulator 100, etc.) operational status, tissue (e.g., tissue 209, etc.) status/ damage, and/or the like, such as by monitoring an impedance associated with an electrode/tissue interface at which the electrode(s) records an electrical signal indicative of a corresponding tissue impedance. Notably, an increased impedance (e.g., beyond a threshold level) can indicate that an electrode is no longer functioning. If high impedance (above the threshold level) is determined, corrective actions can comprise, reprogramming or reconfiguring the tissue stimulator to alleviate redundancy (e.g. 2 channels of an electrode performing in a same manner, etc.), and/or explanting and replacing a failed electrode.

A user can use the GUI to generate stimulus pattern information that is transmitted to the flexible implantable tissue stimulator 100. For example, the pattern information can comprise biphasic charge-balanced simulation with adjustable pulse amplitude and timing. Biphasic charge-balanced simulation is required for avoidance of tissue damage that can potentially be caused by repeated use of a flexible implantable tissue stimulator. Charge-balance can be achieved by alternate methods. For example, charge-balance can be achieved by actively driving current in an opposite direction from a first stimulus phase of stimulus pattern information, or charge-balance can be achieved by passive recovery where electrodes are shorted after a first stimulus phase of stimulus pattern information and excess charge is drained (e.g., bleeding off the excess charge, etc.). The stimulus pattern information can be transmitted to the flexible implantable tissue stimulator 100 to induce muscle contractions in the tissue 209.

The flexible implantable tissue stimulator 100 can comprise an inductive power transceiver 101. Optionally, the inductive power transceiver 101 can be a printed nanoparticle ink coil. The inductive power transceiver 101 can enable bidirectional communication (e.g., wireless communication, radio frequency (RF) communication, amplitude modulated signals, etc.) and power transmission (e.g., inductive power transmission, rechargeable power transmission, etc.) between the flexible implantable tissue stimulator 100 and the computing device 201. The inductive power transceiver 101 can receive power (e.g., an inductive voltage, etc.) from the power and transceiver module 202 via the inductive coil 206. For example, the computing device 201 (power and transceiver module 202) can generate magnetic fields that induce the inductive power transceiver 101 to generate voltage.

The flexible implantable tissue stimulator 100 can comprise a pattern generation module 107. Pattern generation data can be generated by the computing device 201 (the control module 203), transmitted by the power and transceiver module 202, and received by the inductive power transceiver 101. The pattern generation data can be provided to the pattern generation module 107. For example, the pattern generation data can cause the pattern generation module 107 to generate biphasic charge-balanced stimulation patterns with adjustable amplitude and timing. The pattern generation module 107 can comprise dedicated application-specific integrated circuits (ASICs), which can be provided in the form of pattern generation nodes 102 as disclosed herein. The pattern generation module 107 can comprise type of integrated circuit or the like suitable for generating user defined pulse stimulation patterns. The pattern generation module 107 can comprise one or more integrated circuits that operate independently or synchronously, or both independently and synchronously depending on user selection/input. The pattern generation module 107 can generate one or more patterns based on muscle stimulation pattern information received from the computing device 201. For example, the one or more patterns can correspond to one or more asynchronous electrical stimulation pulses generated by the pattern generation module 107 at any frequency (e.g., 20 Hertz, etc.) and/or duty cycle (e.g., a 15-second on, 15-second off pulse stimulation with a 17 minute rest interval, etc.). The flexible implantable tissue stimulator 100 can comprise operational current amplifiers (not shown) that increase currents of one or more patterns generated by the pattern generation module 107.

As previously described, the flexible implantable tissue stimulator 100 can comprise electrodes 103. The electrodes 103 can be intramuscular electrodes. The electrodes 103 can comply with industry standards. For example, the electrodes 103 can comprise IS-1 type connector ports, DF-1 type connector ports, combinations thereof, or the like. One or more patterns generated by the pattern generation module 107 can correspond to one or more electrical pulses transmitted by the electrodes 103 to stimulate the tissue 209. The tissue 209 can be any type of tissue, such as gluteal muscle tissue and/or the like. For example, the electrodes 103 can be placed in close proximity and/or touching a motor point or a nerve associated with the tissue 209. The close proximity placement of the electrodes 103 can reduce a level of electrical charge required to stimulate the nerve (tissue 209). A reduced electrical charge requirement can enable the flexible implantable tissue stimulator 100 to operate with minimal power consumption. Minimal power consumption enables the flexible implantable tissue stimulator 100 to be reliable and simple to use long-term, on a day-to-day basis, to maintain hypertrophy of impaired tissue, such as paralyzed gluteal muscles (e.g., the tissue 209, etc.), for example.

Figure 3A:
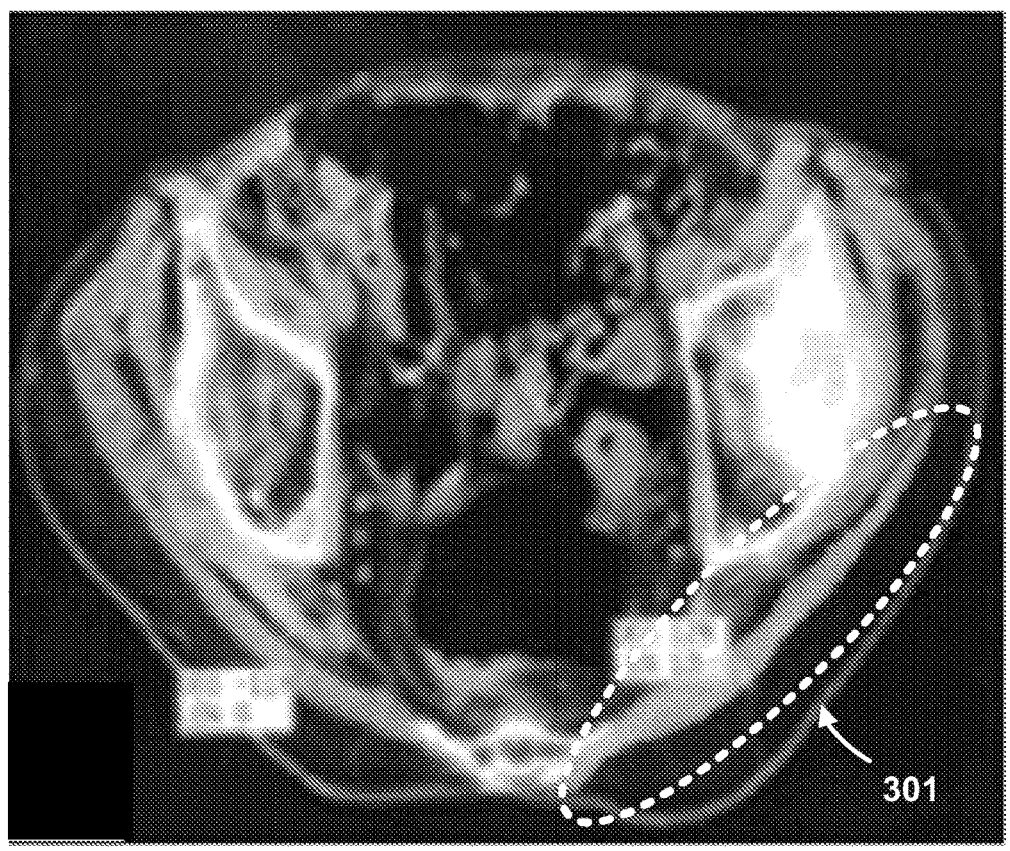
FIG. 3A depicts an image of gluteal muscle thickness of an individual following an SCI.
Figure 3B:
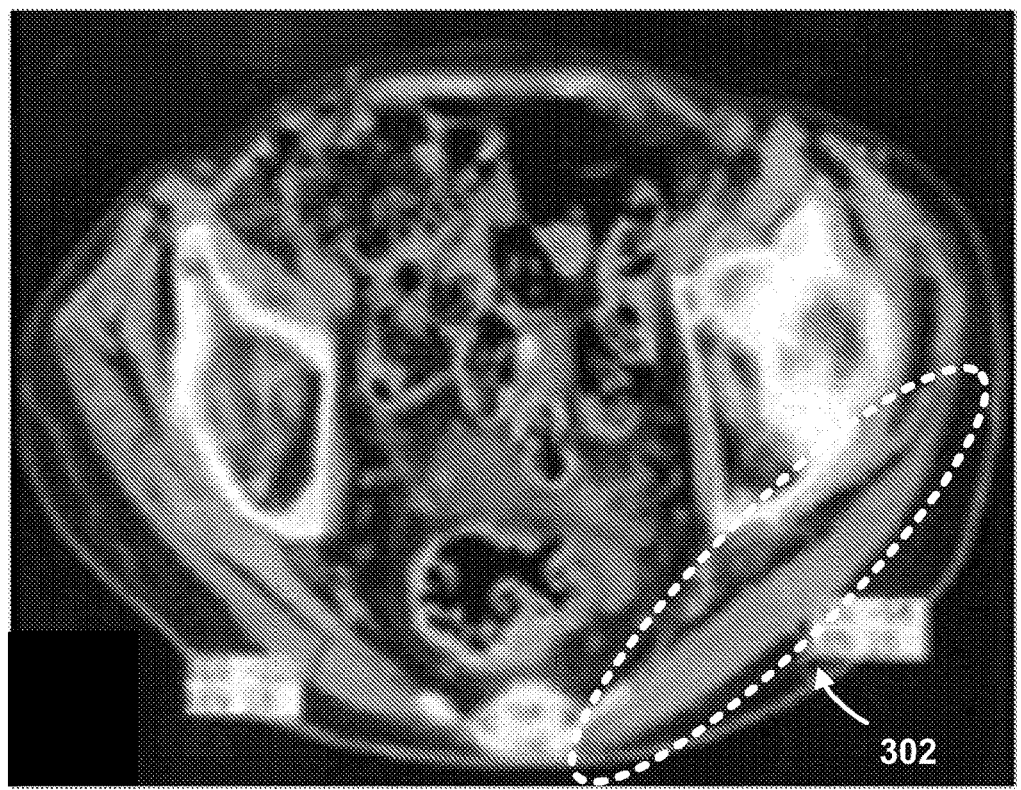
FIG. 3B depicts an image of gluteal muscle thickness of the individual following six weeks of electrical stimulation.

FIGS. 3A-3B depict the results from testing a flexible implantable tissue stimulator. In a patient, such as a patient that has suffered a spinal cord injury (SCI), an inferior gluteal nerve lies relatively deep to the buttock surface and close to the sciatic nerve. Regular use of electrical stimulation (ES) via a flexible implantable tissue stimulator can produce changes in stimulated muscles that increase soft tissue health. FIG. 3A and FIG. 3B both depict a transverse computed tomography section through the top of head of the femur. A gluteal muscle thickness of an individual that suffered an SCI is showed in the region 301 of FIG. 3A. The region 302 in FIG. 3B shows a significant increase (approximately fifty percent) in gluteal muscle thickness of the individual after using a flexible implantable tissue stimulator to provide intermittent electrical stimulation for a six-week period.

Figure 4:
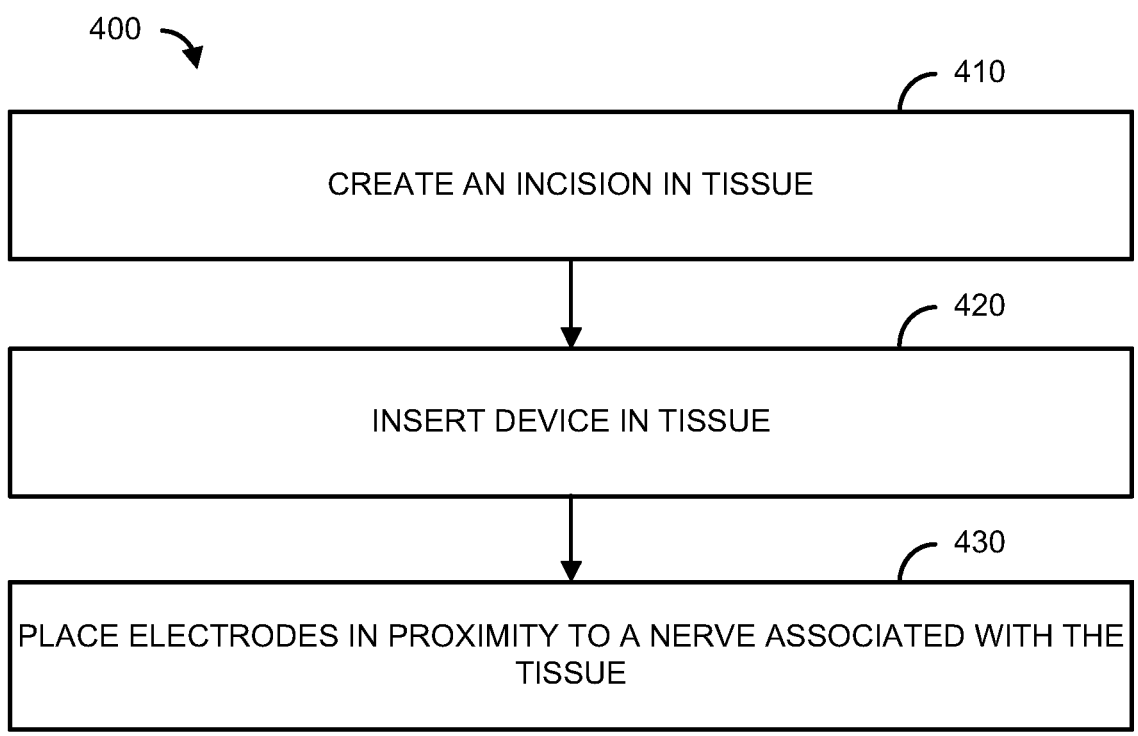
FIG. 4 is a flowchart of an example method for using a flexible implantable tissue stimulator as disclosed herein.

FIG. 4 is a flowchart of an example method 400 for using a flexible implantable tissue stimulator 100. At 410 a medical professional (e.g., surgeon) can create a surgical incision in tissue. Different types/locations of surgical incisions in tissue can be made in various tissue types, such as in a gluteal muscle region. The surgical incision can be small, such as about 25.5 millimeters (one inch). However, it is understood that the surgical incision can be any suitable length. The surgical incision can be large enough to receive a flexible implantable tissue stimulator with dimensions of a length between 0 millimeters and 24 millimeters, a width between 0 millimeters and 12 millimeters, and a height (e.g., thickness, etc.) between 0 millimeters and 4 millimeters.

At 420, the medical professional can advance (either manually or via automated surgical devices) a flexible implantable tissue stimulator into the surgical incision.

At 430, electrodes of the flexible implantable tissue stimulator can be placed in close proximity and/or touching a nerve (motor point) associated with the tissue. The close proximity placement of the electrodes can reduce a level of electrical charge required to stimulate the nerve. A reduced electrical charge requirement enables the flexible implantable tissue stimulator to operate with minimal power consumption. Minimal power consumption enables the flexible implantable tissue stimulator to be reliable and simple to use long-term, on a day-to-day basis, to maintain hypertrophy of the tissue.

Exemplary Surgical Procedure for Disclosed Flexible Implantable Tissue Stimulators Provided is an example surgical procedure for a flexible implantable tissue stimulator. A subject may undergo pre-screening and preparation prior to implantation of a flexible implantable tissue stimulator. For example, approximately two days prior to a scheduled implantation procedure the subject can be contacted to review eligibility for implantation and verify an applicable consent form has been completed by the subject. It can be verified that there has been no change in a medical status of the subject since consent was obtained and that the subject does not have an active urinary tract infection, open wound, or significant active systemic disease that has not disclosed. The subject can indicate a location preference (e.g., of a left side, on a right side, etc.) for placement of the flexible implantable tissue stimulator. If consent for the procedure has not been previously obtained, the subject can provide consent on the day of the procedure. Any change in medical status or outstanding issues that could impact the implantation procedure must be resolved prior to implanting the flexible implantable tissue stimulator in the subject. An implantation procedure can be postponed until all issues are resolved, such as urinary tract infection (UTI) issues, and the like.

On a day of an implantation procedure, all consent forms and implantation locations must be verified. Upon verification, the subject can be led to a Surgical Procedure Room, dressed in a surgical gown, and transferred to a theater table. The subject can be placed in a lateral decubitus position, lying on the contra-lateral side to the implantation site of the flexible implantable tissue stimulator (e.g., a right side is a flexible implantable tissue stimulator will be on a left side of the subject).

Figure 5A:
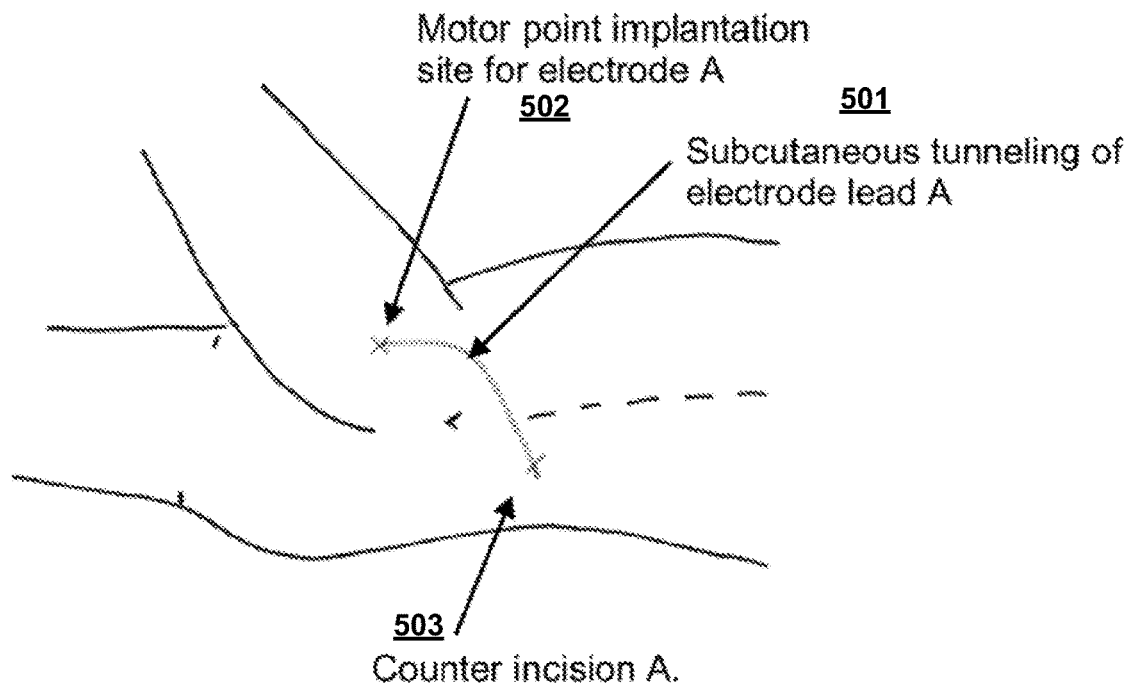
FIGS. 5A-5H depict exemplary surgical procedures for implanting a flexible implantable tissue stimulator in a subject.

FIGS. 5A-5H illustrate a procedure implanting a flexible implantable tissue stimulator in a left flank of a subject. Notably, illustrated sides/portions of the subject would be reversed for a right side location/implantation. The right side of the subject is referenced herein as side A, and the left side of the subject referenced herein as side B. FIG. 5A illustrates passing an electrode (electrode A) of a flexible implantable tissue stimulator to a counter-incision (e.g., counter incision A). Hips and knees of the subject can be flexed to approximately 90 degrees and the buttock and lower back region can be swabbed with Betadine and draped using sterile surgical drapes.

A gluteal region of side A can be probed for a strongest stimulation response. For example, the gluteal region can be probed with an intra-muscular (IM) mapping probe. Once the strongest stimulation response location is identified, 2% Lidocaine can be injected along a tunneling route 501 from a motor point implantation site 502 for an electrode of the flexible implantable tissue stimulator (e.g., electrode A) to a counter incision site A at 503.

An outer sheath can be placed over the mapping probe and aligned to ensure positioning at a correct (e.g., desired, etc.) depth. The mapping probe can be later removed and a lead carrier loaded with electrode A of the flexible implantable tissue stimulator can be introduced. A stimulation response induced by the electrode A can be tested to verify that it is the same as the probe response. If a reduced response is obtained the probing procedure can be repeated. The outer sheath and lead carrier can then be removed, leaving the electrode A implanted in the desired location.

The counter incision A (503) can be created above the posterior iliac crest on side B (left side) of the subject. The tunneler can be introduced from the counter incision A (503) and tunneled to implantation site A (502).

Suction can be used to pass the electrode lead A (implanted at site 509), of the flexible implantable tissue stimulator through to counter-incision A (503) using suction. The electrode A can be tested to ensure a continued good response. The tunneler can be withdrawn so that electrode lead A exits the counter incision site A at 503.

Figure 5B:
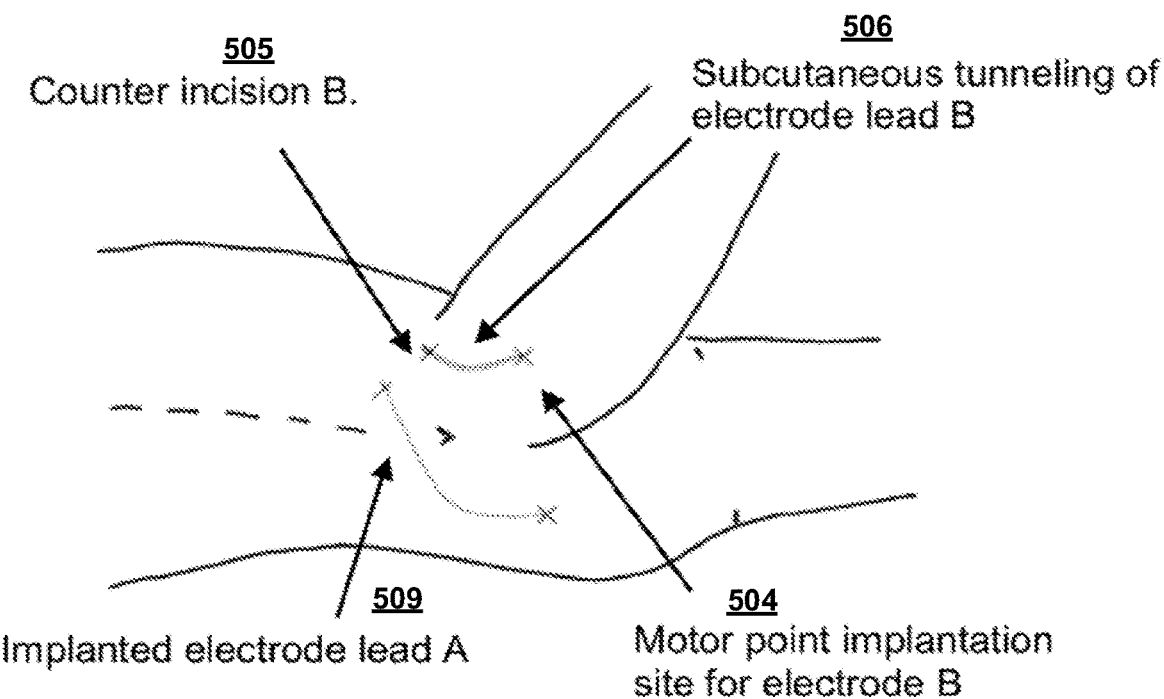

FIG. 5B illustrates passing an electrode (electrode B) of the flexible implantable tissue stimulator to a counter-incision on a left side of the subject. The subject can be carefully rolled to the other side (e.g., left side) and placed in a lateral decubitus position on the ipsilateral side to a motor point implantation site 504 of the flexible implantable tissue stimulator. Care must be taken to maintain a sterile field over a lower back region and a counter incision site 505. The hips and knees of the subject can be flexed to approximately 90 degrees and the buttock and lateral flank of the subject can be swabbed with Betadine and draped using sterile surgical drapes.

A gluteal region of side B can be probed for a strongest stimulation response using the IM mapping probe. Upon locating the strongest stimulation response, 2% Lidocaine can be injected along a tunneling route 506 from implantation site for electrode B to counter incision site B. An outer sheath can be placed over the mapping probe and aligned to ensure positioning at the correct depth. The mapping probe can be removed and the lead carrier loaded with electrode B is introduced. A stimulation response using electrode B of the flexible implantable tissue stimulator can be tested to verify that it is the same as the probe response. If a reduced response is obtained the probing procedure can be repeated.

Upon locating the strongest stimulation response, 2% Lidocaine can be injected along the tunneling route 506 from the motor point implantation site 504 for electrode B to the counter incision site B (505). Counter incision B (505) can be created above the posterior iliac crest on side B (left side) of the subject, 2-3 centimeter lateral and 1-2 centimeter distal to counter incision A (503). The tunneler can be introduced from counter-incision B (505) and carefully tunneled to implantation site B (504). Suction can be used to pass an electrode lead B of the flexible implantable tissue stimulator through to the counter-incision B (505). The electrode B can be tested to ensure a continued good response. The tunneler can be withdrawn so that electrode lead B exits counter-incision B (505).

Figure 5C:
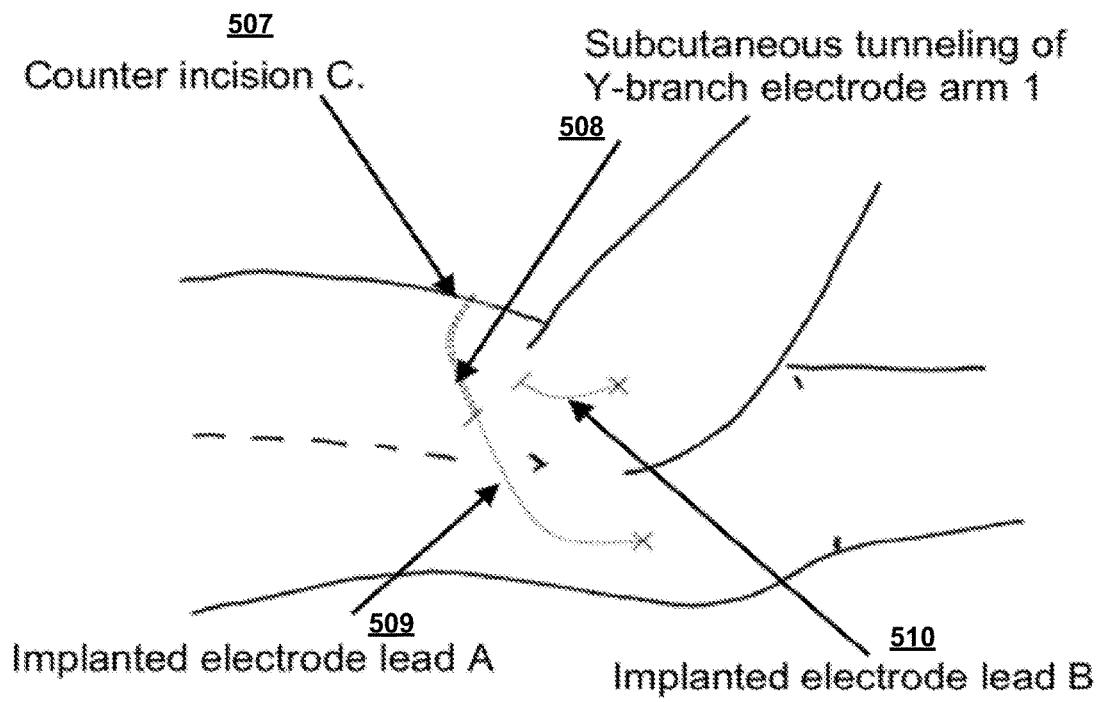
Figure 5D:
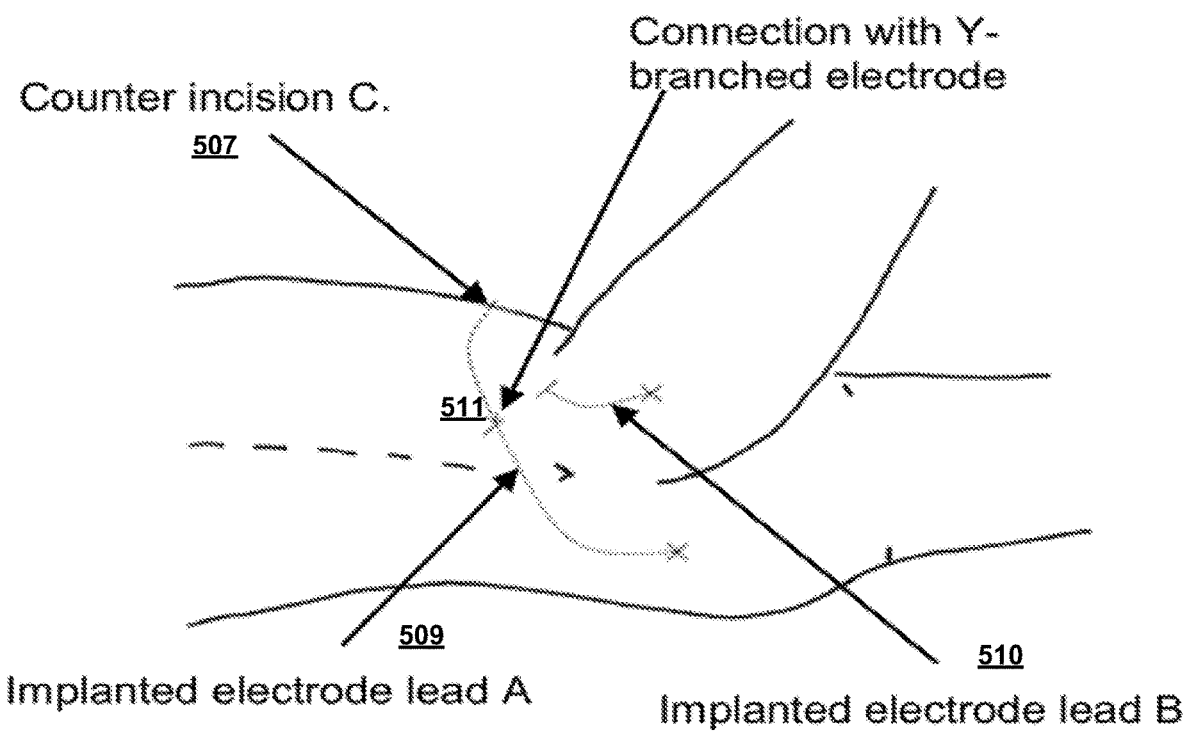

FIG. 5C illustrates electrode A of the flexible implantable tissue stimulator connected to a first arm (arm 1) of a Y-branch electrode (electrode of the flexible implantable tissue stimulator). A counter incision C (507) can be created over lateral iliac crest of the subject. The counter incision C (507) can be 5-10 centimeters lateral from counter incisions A (503) and B (505). The tunneler can be introduced from counter-incision C (507) and carefully tunneled to counter incision A (503). Suction can be used to pass arm 1 of the Y-branched electrode through to counter-incision A (503). The tunneler can be withdrawn so that one arm of the Y-branched electrode exits the counter-incision A (503). As shown in FIG. 5D, at 511 the arm of the Y-branched electrode interconnect can be connected to electrode A. FIG. 5C illustrates an electrode A of the flexible implantable tissue stimulator connected to arm 1 of a Y-branch electrode.

FIG. 5D illustrates passing arm 2 of the Y-branch electrode to counter incision B (505). The tunneler can be re-introduced from counter-incision C (507) and carefully tunneled at 508 to counter incision B (505). Arm 2 of the Y-branched electrode interconnect is passed through to counter-incision B (505) using suction. The tunneler can be withdrawn so that arm 2 of the Y-branched electrode exits counter-incision B (505). Electrode lead A of the flexible implantable tissue stimulator can be implanted in the subject at site 509. Electrode lead B of the flexible implantable tissue stimulator can be implanted in the subject at site 510.

Figure 5E:
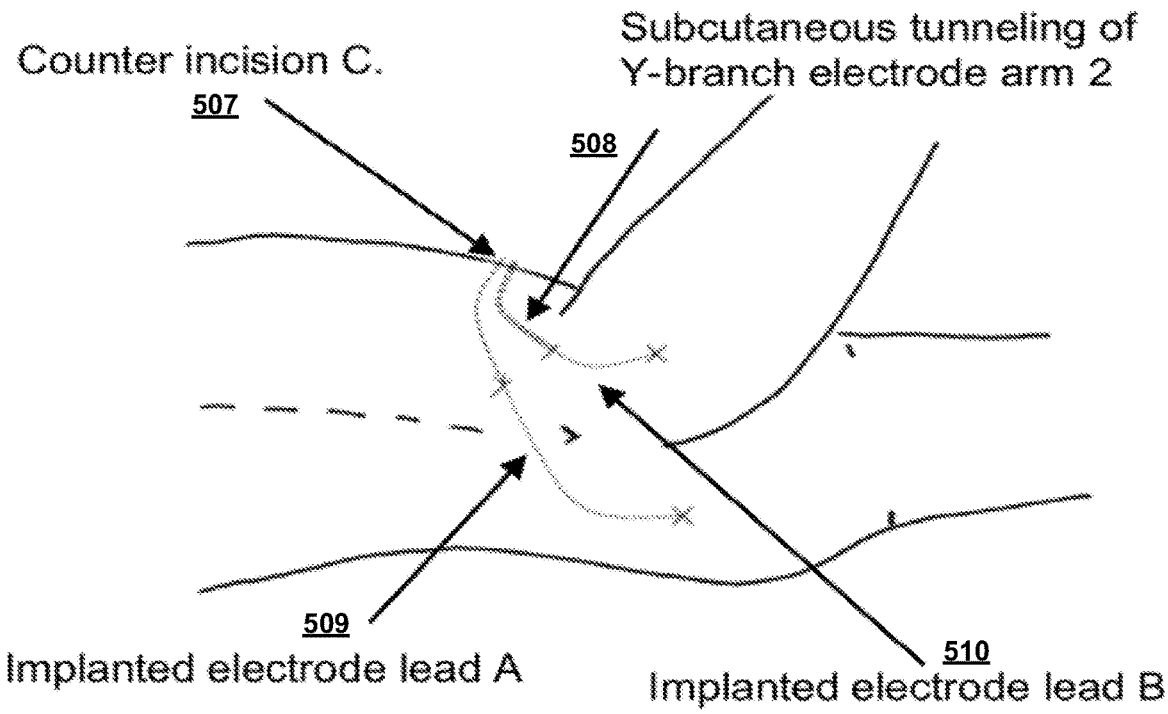
Figure 5F:
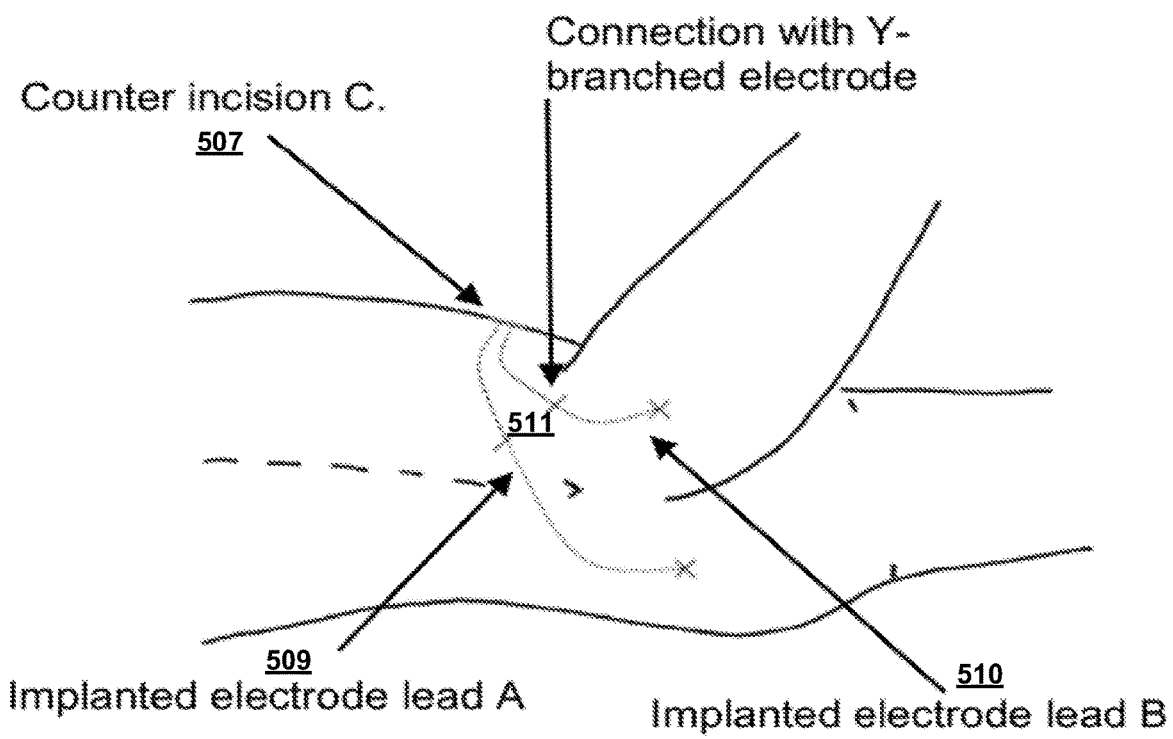

FIG. 5E illustrates passing arm 2 of the Y-branch electrode to counter-incision B (505). Arm 2 of the Y-branched electrode interconnect can be connected to electrode B of the flexible implantable tissue stimulator. FIG. 5F illustrates electrode B of the flexible implantable tissue stimulator connected to arm 2 of the Y-branch electrode (511).

Figure 5G:
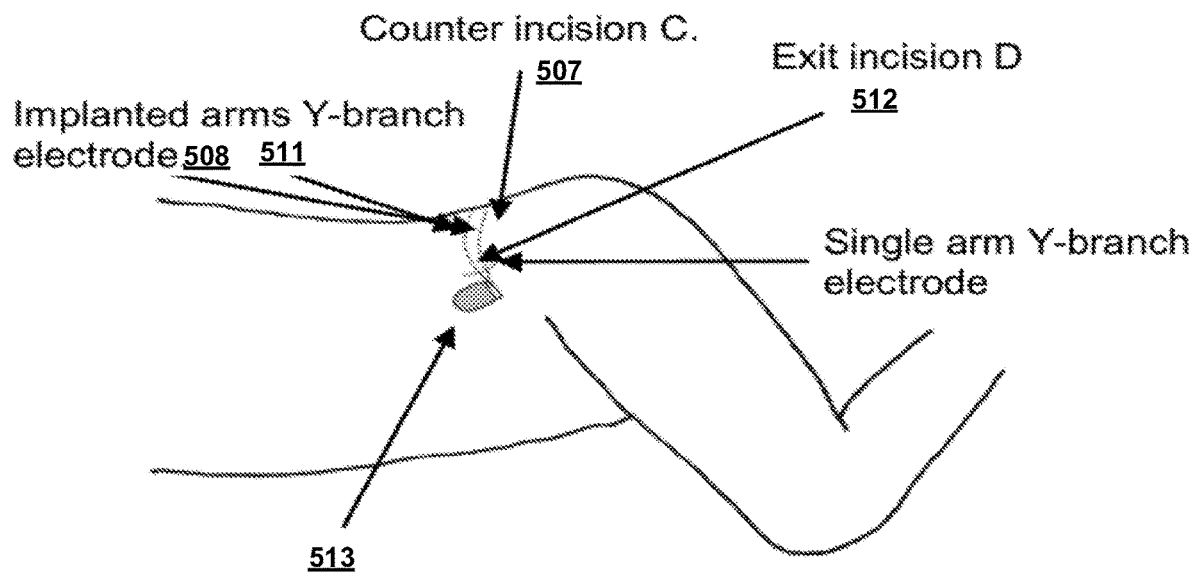
Figure 5H:
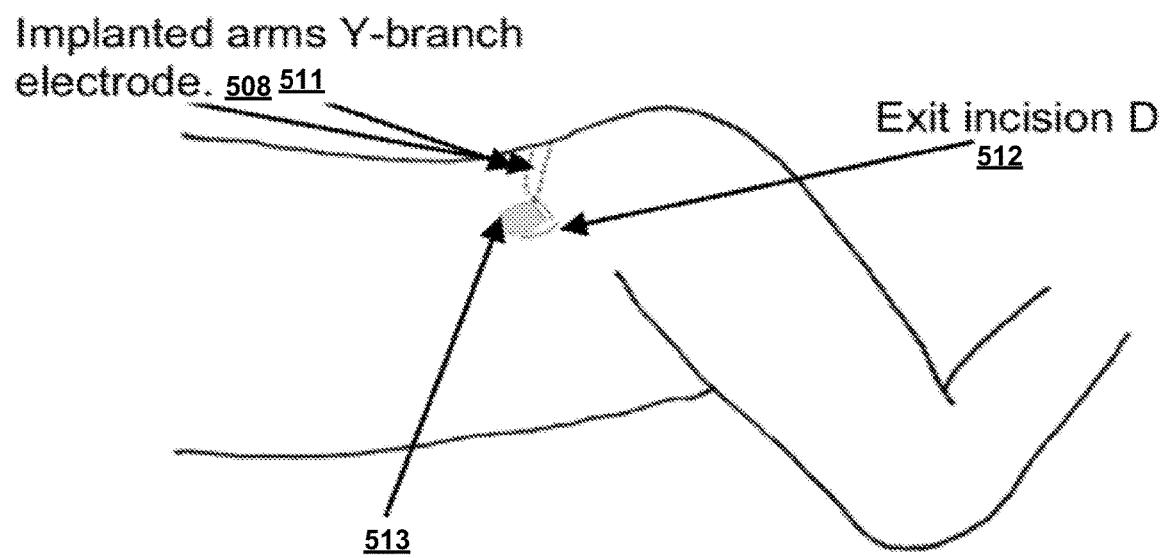

FIG. 5G illustrates a single arm of the Y-branch electrode passed through an incision. Hip and knee flexion are can be slightly reduced and the subject can be carefully rolled to expose a side of the abdomen. A 3 to 5 centimeter exit incision D (512), is made over the lower abdominal region and a small pocket created subcutaneously by separation of the subdermal layer. The tunneler can be introduced from exit incision D (512) and carefully tunneled to counter incision C (507). Suction can be used to pass the single arm of the Y-branched electrode interconnect through to exit incision D (512).

The single arm of the Y-branch electrode can be connected to the flexible implantable tissue stimulator 513. Electrodes A and B can be tested to ensure a continued good response from stimulation from the flexible implantable tissue stimulator 513. An extra length of the Y-branch electrode and the flexible implantable tissue stimulator 513 can be tucked in a subcutaneous pocket. All incisions can be closed using 4-0 Vicryl. Steri-strips and Telfa dressings can be applied. FIG. 5G illustrates a flexible implantable tissue stimulator (513) implanted in the subject with all incisions closed.

Exemplary Uses of the Disclosed Flexible Implantable Tissue Stimulators

In use, it is contemplated that long-term use of a flexible implantable tissue stimulator as disclosed herein can provide an effective adjunctive method for achieving a regular pressure relief regimen in high-risk individuals. It is further contemplated that long-term application of reliable and repeatable dynamic electrical stimulation as disclosed herein can improve the intrinsic properties of paralyzed muscle levels in persons with long-standing SCI through contractile responses to repeated stimulation, thereby reducing the risk of PU/DTI development and allowing users to participate more fully in activities of daily living (ADL) with minimal effort.

In exemplary aspects, it is contemplated that the disclosed flexible implanted tissue stimulator can provide a plurality of channels (e.g., four channels) of independently controlled electrical stimulation in a seamless package that is compact, biocompatible, mechanically biomimetic and uses MRI compatible materials. It is contemplated that the construction of the flexible implanted tissue stimulator can enable placement of the device in areas of the body with limited soft tissue coverage with reduced risk of erosive tissue damage. It is further contemplated that implantation procedures will be minimally invasive, so that the disclosed flexible implanted tissue stimulator can be implemented as an outpatient procedure, thus making it accessible to many more clinicians and end-users. It is further contemplated that stable and reliable dynamic MRI compatibility can enable users to have access to advanced imaging if it becomes medically necessary.

In use, the fully implanted tissue stimulator can provide effective PU/DTI prevention by delivery of regular and effective weight shifting throughout the day and on demand without repetitive user effort. It is contemplated that daily use can augment the user's PU/DTI prevention efforts, providing automatic weight-shifting every 20 minutes with minimal ADL disruption and enhanced maintenance of tissue health, alleviating the requirement for manual pressure relief every 15-20 minutes as is required with existing systems.

In exemplary aspects, it is contemplated that advanced fabrication techniques can be used to combine flexible hybrid electronics (FHE), dedicated application-specific integrated circuits (ASICs) chips and discrete components on a flexible liquid crystal polymer (LCP) substrate, and to encapsulate the core in a seamless multi-layer polymeric package, thereby producing a flexible implantable tissue stimulator as disclosed herein.

In one exemplary configuration, four channels of 20 Hz electrical stimulation can produce active weight-shifting using commercially available bilateral IM electrodes to deliver stimulation for 3 minutes with a variable duty cycle (e.g., 15 second on, 15 second off) followed by a 17 minute rest period. Data and power can be transmitted by a bidirectional inductive link delivering power and transmitting/receiving data. The disclosed system can wirelessly monitor electrode and power supply voltages, as well as outbound or 'reverse' telemetry to check for data transmission errors. In exemplary configurations, the disclosed stimulator will not contain an internal batter; thus, in these configurations, charging cycles for the external controller battery will depend on the stimulation duty cycle commanded. It is contemplated that the disclosed stimulator can have an onboard electrode and power supply voltage monitoring capability (using conventional sensing/monitoring components), as well as outbound or 'reverse' telemetry to check for data transmission errors. Data and power can be transmitted bi-directionally by an inductive link as further disclosed herein.

In exemplary aspects, it is contemplated that the pattern generation nodes of the stimulator can comprise ASIC chips which receive inbound data by a FSK demodulator, and/or a delay-locked loop circuit. As the data are received, a cyclic redundancy check (CRC) can be performed, and bad data packets can be discarded.

In exemplary aspects, an RF communication and power link to the chip can operate on a carrier that is delivered via an external primary coil. A primary coil can create magnetic fields that in turn induce voltage in the implanted secondary coil. The inbound magnetic field can be frequency shift keyed (FSK) to encode the input data at any rate, such as 565 Kbps, for example. Outbound diagnostic data generated by the stimulator can draw excess current from the secondary coil, using load shift keying, which allows transmission of outbound data using very little power. The FSK modulation can be performed by switching the frequency tuning components in the transmitter circuit. It is contemplated that this disclosed configuration can provide robust power transmission and bidirectional telemetry with an end-to-end power efficiency of more than 10% at up to 25 millimeter separation between coils. The primary coil diameter can be about 50 mm, including silicone over-molding to protect the coil and the user. In use, this coil can experience little or no heating above body temperature, and is further reduced by the active duty cycle as disclosed herein and a small separation distances (which will generally be less than 15 millimeters). The implanted secondary coil can be packaged in multi-layered PDMS/parylene. With optimal impedance matching of the secondary coil to the implanted circuitry, the received power can be equally dissipated in the coil and the ASIC circuit. It is contemplated that the secondary coil can comprise low power dissipation (e.g., less than 2 mW) while actually stimulating (note the low duty cycle). This minimal heating can be easily dissipated by the body. In use, there can be strong coupling between the primary and secondary coils due to the short distance. Any slight misorientations can be robustly accommodated because transmitted power can adjust dynamically to support the desired ASIC supply voltage via the RF telemetry link. It is contemplated that the transmitted power will fall off with the cosine of the angle between the coils. Effective power supply management via the telemetry link will be crucial for overall efficiency and battery life, saving system power and heat dissipation when stimuli are few or absent and compensating for movement without requiring a system reset in the event of power fluctuations. Thus, it is contemplated that these disclosed power and data transmission capabilities will be more than adequate for the transmission distances anticipated for the disclosed stimulators and systems.

In exemplary aspects, the electronics circuit may incorporate off-chip operational current amplifiers to increase output currents from the ASIC to appropriate IM stimulation current levels. To avoid over-stimulation, hardware and software limits can prevent total electrode charge from exceeding safe values according to both electrochemical and biological safety limits. Independent circuits can monitor the electrode voltages to ensure that they do not exceed the 'water window' voltage limit. The electrodes can be shorted to ground between pulses to resolve any residual polarization and independent circuits can monitor the electrodes to ensure grounding.

In one exemplary manufacturing process, and as further disclosed herein, additive manufacturing techniques can be used to create an implantable, biocompatible, FHE core with a LCP substrate and MRI-compatible silver nanoparticle inks. It is contemplated that circuitry components including inductive coils and other passive devices can be printed using a Direct Write Electronics (DWE) Additive Manufacturing (AM) approach. The DWE methods can include, for example and without limitation: aerosol-based print technologies, syringe print extrusion methods, thermoplastic printing, ink jet printing, or co-extrusion of polymer/conductor materials. These DWE approaches can be used individually or together to create an optimum circuit and/or to provide transition features needed to print electronic features over normally discrete discontinuous surfaces or planes. The suit of DWE inks can include nanoparticle-based conductors and dielectrics such as Ag, Ag, Ni, Pt, Al2O3, etc., flake based metallic conductors captured in a printable slurry, or solution based inks for conductors and dielectrics. The DWE materials may require post process treatment to activate the materials or can include methods such plasma sintering to provide fully activated structure upon completion of printing Dedicated ASICs and discrete components can be placed in a distributed layout to optimize physical flexibility. The DWE methods can be used to create circuitry and to interconnect between circuitry on discrete devices placed on the FHE substrate. The FHE core can be encapsulated and packaged using a multilayer conformal coating of parylene-C, medical-grade epoxy, and PDMS.

In exemplary aspects, it is contemplated that AJ Direct Write™ electronics printing technology can be used to the stimulator circuitry (including inductive coils and conductive circuit traces) onto the flexible substrate. The Direct Write™ technology software can provide the ability to cure and reregister circuitry for subsequent deposition. MRI compatible silver nanoparticle inks can be used for the traces and secondary antennae/induction coil.

In exemplary aspects, the ASIC chips and discrete components can be placed in a distributed layout to optimize the mechanical flexibility of the overall system. More particularly, these components can be bonded onto the LCP substrate and interconnect with the printed circuitry. The populated FHE core can be coated with an initial deposition layer of parylene-C by conventional vapor deposition before packaging. If added mechanical protection is necessary for components of the FHE core, medical-grade epoxy can be applied to these components locally by drop casting or related deposition techniques. As an example, the parylene-C can be applied after epoxy dispensing.

Optionally, the disclosed stimulator can be packaged using multiple thin layers of pressure densified PDMS alternated with parylene-C to achieve a final packaged device thickness of about 4 millimeters (or other selected thickness). The packaging process can be initiated in a Class 100 cleanroom. The IS-1 connector ports can be capped during conventional cleaning procedures. The devices can be rinsed in baths of isopropyl alcohol and deionized water in sequence with ultrasonic agitation. The resistivity of each cleaning bath can be monitored during rinsing. The solution can be changed every 15 minutes. The cleaning process can be complete when the measured solution resistivity exceeds 70% of its original value for more than 5 minutes. Function of the disclosed stimulators can then be evaluated to exclude unacceptable devices. PDMS can be deposited by the centrifugal-force casting method. This process can begin by placing each device and a prescribed amount of PDMS into standard test tubes, which are loaded into a centrifuge and spun at 1700 rpm for 10 minutes. Devices can then be moved to a second set of test tubes and spun for an additional 3 min at 1700 rpm to remove excess PDMS thus ensuring a uniform coating. Coated samples can then be degassed and vacuum cured at 70 degrees Celsius for 30 minutes. The casting and curing steps can be repeated until the desired coating thickness is achieved. The combination of centrifugal-force casting and vacuum curing can create a uniform coating of the highest possible density and minimal volumetric defects, which significantly increases moisture barrier properties. The multilayered structure can also significantly enhance the moisture barrier properties by providing interfaces that serve to terminate penetrating defects.

In further exemplary aspects, it is contemplated that various standards for the disclosed stimulator can be confirmed using conventional methods. For example, ethylene oxide sterilization can be validated to ISO 10993-7:2008 standards, package bio-stability can be evaluated in accelerated lifetime tests under simulated in vivo conditions, and MRI compatibility can be characterized using F2052 and F2213 ASTM testing standards.

Exemplary Aspects

In view of the described devices, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A device comprising: an inductive power transceiver; one or more pattern generation nodes in communication with the transceiver, wherein the one or more pattern generation nodes generate one or more patterns based on muscle stimulation pattern information received from the transceiver; and one or more electrodes in communication with the one or more pattern generation nodes, wherein the one or more electrodes receive electronic pulses that correspond to the one or more patterns.

Aspect 2: The device of aspect 1, wherein the inductive power transceiver is in communication with a control device comprising a power supply, wherein the transceiver receives an inductive power transfer from the power supply.

Aspect 3: The device of aspect 2, wherein the power supply is rechargeable.

Aspect 4: The device of any one of aspects 1-3, wherein each pattern generation node of the one or more pattern generation nodes comprises an application-specific integrated circuit (ASIC).

Aspect 5: The device of any one of aspects 1-4, further comprising a substrate having a flexural modulus of less than 200 MPa.

Aspect 6: The device of any one of aspects 1-5, wherein the one or more pattern generation nodes are in communication with the transceiver via silver nanoparticle ink trace on the substrate, wherein the substrate is a liquid crystal polymer (LCP) substrate.

Aspect 7: The device of any one of aspects 1-6, wherein the one or more electrodes are in communication with the one or more pattern generation nodes via silver nanoparticle ink trace on the substrate.

Aspect 8: The device of any one of aspects 1-7, wherein the device is coated with parylene-C via vapor deposition.

Aspect 9: The device of any one of aspects 1-8, wherein the device is encapsulated in one or more layers of polydimethylsiloxane.

Aspect 10: The device of any one of aspects 1-9, wherein the device comprises a length between 0 millimeters and 24 millimeters, a width between 0 millimeters and 12 millimeters, and a height between 0 millimeters and 4 millimeters.

Aspect 11: The device of any one of aspects 1-10, wherein the inductive power transfer is based on a frequency shift keyed magnetic field, and the transceiver provides data to the one or more pattern generation nodes at a rate of at least 565 Kbps.

Aspect 12: The device of any one of aspects 1-11, wherein the transceiver communicates wirelessly with one or more of a computing device or a display device.

Aspect 13: The device of any one of aspects 1-12, wherein the one or more patterns are generated according to one or more of a predefined time period or a duty cycle.

Aspect 14: The device of any one of aspects 1-13, wherein the one or more intramuscular electrodes each comprise a distal end that provides the electronic pulses to muscle tissue.

Aspect 15: A method comprising: creating an incision in a gluteal region; implanting a device of any one of aspects 1-14; and using the device to electronically stimulate gluteal muscle tissue.

Aspect 16: The method of aspect 15 further comprising transmitting, to a display device, muscular functional information associated with the stimulated muscle tissue.

Aspect 17: The method of aspect 16, wherein the display device comprises a graphical user interface (GUI).

Aspect 18: A system comprising: a control module configured to: receive, via a graphical user interface, muscle stimulation pattern information, transmit one or more signals comprising the muscle stimulation pattern information, and generate one or more magnetic fields; a muscular stimulation device configured to: receive, via a transceiver, the one or more magnetic fields, wherein the one or more magnetic fields cause the transceiver to generate voltage; receive the one or more signals comprising the muscle stimulation pattern information, generate, based on the muscle stimulation pattern information, one or more patterns, and cause, based on the one or more patterns, one or more electrodes to transmit one or more electrical pulses that correspond to the, one or more patterns; and the one or more electrodes.

Aspect 19: The system of aspect 18, wherein the transceiver is an inductive power transceiver.

Aspect 20: The system of any of aspects 18-19, wherein the one or more signals comprise one or more radio frequency (RF) signals.

Aspect 21. The system of any of aspects 18-20, wherein the muscular stimulation device further comprises a rechargeable power source.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in a generic and descriptive sense, and not for the purposes of limiting the described invention.

What is claimed is:

1. A device configured for implantation within a body of an individual, the device comprising:
   an inductive power transceiver, wherein following implantation of the device within the individual, the inductive power transceiver is configured for communication with a power supply of an external device that is positioned outside the body of the individual, wherein the inductive power transceiver is configured to receive an inductive power transfer from the power supply;
   a plurality of pattern generation nodes in communication with the inductive power transceiver, wherein the plurality of pattern generation nodes comprise respective application specific integrated circuits (ASICs) that are each configured to provide a respective channel of independently controlled stimulation, wherein the plurality of pattern generation nodes are configured to selectively operate independently or synchronously to generate one or more patterns based on muscle stimulation pattern information received from the inductive power transceiver;
   a plurality of electrodes in electrical communication with the plurality of pattern generation nodes via conductors, wherein the plurality of electrodes are configured to receive electronic pulses that correspond to the one or more patterns;
   a substrate, wherein the inductive power transceiver is printed on the substrate, wherein the respective application specific integrated circuits of the plurality of pattern generation nodes are coupled to the substrate; and
   a flexible material, wherein the inductive power transceiver and the respective application specific integrated circuits of the plurality of pattern generation nodes are encapsulated together within the flexible material.

2. The device of claim 1, wherein the power supply is rechargeable.

3. The device of claim 1, further comprising a substrate having a flexural modulus of less than 200 MPa.

4. The device of claim 1, further comprising a polymer substrate having thereon a silver nanoparticle ink trace, wherein the plurality of pattern generation nodes are in communication with the inductive power transceiver via the silver nanoparticle ink trace on the polymer substrate.

5. The device of claim 1, further comprising a substrate having thereon a silver nanoparticle ink trace, wherein the plurality of electrodes are in communication with the plurality of pattern generation nodes via the silver nanoparticle ink trace on the substrate.

6. The device of claim 1, wherein the device is coated with parylene-C via vapor deposition.

7. The device of claim 1, wherein flexible material comprises one or more layers of polydimethylsiloxane.

8. The device of claim 1, wherein the device comprises a length between 0 millimeters and 24 millimeters, a width between 0 millimeters and 12 millimeters, and a height between 0 millimeters and 4 millimeters.

9. The device of claim 1, wherein the inductive power transfer is based on a frequency shift keyed magnetic field, and the inductive power transceiver provides data to the plurality of pattern generation nodes at a rate of at least 565 Kbps, wherein the muscle stimulation pattern information comprises amplitude and timing of biphasic charge-balanced muscle simulation.

10. The device of claim 1, wherein the inductive power transceiver is configured to communicate wirelessly with one or more of a computing device or a display device.

11. The device of claim 1, wherein the plurality of pattern generation nodes are configured to generate one or more patterns according to one or more of a predefined time period or a duty cycle.

12. The device of claim 1, wherein the plurality of electrodes each comprise a distal end that provides the electronic pulses to muscle tissue.

13. The device of claim 12, wherein the device defines an end portion, wherein the plurality of electrodes comprise exactly two electrodes that project from the end portion of the device.

14. A method comprising:
creating an incision in a gluteal region;
implanting a device of claim 1; and
using the device to electronically stimulate gluteal muscle tissue.

15. The method of claim 14, further comprising transmitting, to a display device, muscular functional information associated with the stimulated muscle tissue.

16. The method of claim 15, wherein the display device comprises a graphical user interface (GUI).

17. The device of claim 1, wherein the inductive power transceiver at least partially circumferentially surrounds the plurality of pattern generation nodes.

18. A device configured for implantation within a body of an individual, the device comprising:
an inductive power transceiver, wherein following implantation of the device within the individual, the inductive power transceiver is configured for communication with a power supply of an external device that is positioned outside the body of the individual, wherein the inductive power transceiver is configured to receive an inductive power transfer from the power supply;
a plurality of pattern generation nodes in communication with the inductive power transceiver, wherein the plurality of pattern generation nodes comprise respective application specific integrated circuits (ASICs) that are each configured to provide a respective channel of independently controlled stimulation, wherein the plurality of pattern generation nodes are configured to selectively operate independently or synchronously to generate one or more patterns based on muscle stimulation pattern information received from the inductive power transceiver; and
a plurality of electrodes in electrical communication with the plurality of pattern generation nodes via conductors, wherein the plurality of electrodes are configured to receive electronic pulses that correspond to the one or more patterns,
wherein the inductive power transceiver at least partially circumferentially surrounds the plurality of pattern generation nodes.

19. The device of claim 18, wherein the inductive power transceiver completely circumferentially surrounds the plurality of pattern generation nodes.

20. The device of claim 18, further comprising a substrate, wherein the inductive power transceiver is printed on the substrate, and wherein the respective application specific integrated circuits of the plurality of pattern generation nodes are coupled to the substrate.

* * * * *

UNITED STATES PATENT AND TRADEMARK OFFICE
CERTIFICATE OF CORRECTION

| | |
|---|---|
| PATENT NO. | : 11,458,309 B2 |
| APPLICATION NO. | : 16/648031 |
| DATED | : October 4, 2022 |
| INVENTOR(S) | : Christian Zorman et al. |

It is certified that error appears in the above-identified patent and that said Letters Patent is hereby corrected as shown below:

In the Specification

In Column 1, after Line 14, and before the heading FIELD on Line 15, please insert:
--GOVERNMENT SUPPORT CLAUSE
This invention was made with the government support under W81XWH-17-1-0149 awarded by the Department of Defense. The government has certain rights in the invention.--

Signed and Sealed this
Sixteenth Day of January, 2024

*Katherine Kelly Vidal*

Katherine Kelly Vidal
*Director of the United States Patent and Trademark Office*